(12) United States Patent
Wan et al.

(10) Patent No.: US 8,916,607 B2
(45) Date of Patent: Dec. 23, 2014

(54) USE OF PIPERPHENTONAMINE OR SALTS THEREOF IN MANUFACTURE OF MEDICAMENTS FOR TREATING BRAIN DISEASES

(75) Inventors: Huayin Wan, Guangzhou (CN); Rubing Li, Guangzhou (CN); Lijian Zhou, Guangzhou (CN); Tieqiu Liu, Guangzhou (CN); Yangshu Chen, Guangzhou (CN); Yonghe Li, Guangzhou (CN)

(73) Assignee: Guangzhou Municipal Zhongwei Biotechnology Limited Company, Guangdong (CN)

( * ) Notice: Subject to any disclaimer, the term of this patent is extended or adjusted under 35 U.S.C. 154(b) by 101 days.

(21) Appl. No.: 13/498,272

(22) PCT Filed: Oct. 20, 2009

(86) PCT No.: PCT/CN2009/074526
§ 371 (c)(1),
(2), (4) Date: Mar. 26, 2012

(87) PCT Pub. No.: WO2011/035500
PCT Pub. Date: Mar. 31, 2011

(65) Prior Publication Data
US 2012/0184607 A1    Jul. 19, 2012

(30) Foreign Application Priority Data
Sep. 24, 2009    (CN) .......................... 2009 1 0307637

(51) Int. Cl.
*A61K 31/335*    (2006.01)
*A61K 31/36*    (2006.01)
*A61K 31/357*    (2006.01)

(52) U.S. Cl.
CPC ............... *A61K 31/36* (2013.01); *A61K 31/357* (2013.01)
USPC .......................................................... 514/452

(58) Field of Classification Search
CPC .............................. A61K 31/357; A61K 31/36
USPC .......................................................... 514/452
See application file for complete search history.

(56) References Cited

FOREIGN PATENT DOCUMENTS

| CN | 1395923 A | 2/2003 |
|---|---|---|
| CN | 101234102 A | 8/2008 |

OTHER PUBLICATIONS

Mu, Ying et al., Pharmacokinetics Study on Peperphentonamine in Beagle Dogs, Chinese Journal of Hemorheology, 2006, 16(3), p. 338-340, Suzhou Univ. press, Suzhou, China.

*Primary Examiner* — Kevin E Weddington
(74) *Attorney, Agent, or Firm* — Buchanan, Ingersoll & Rooney PC

(57) ABSTRACT

The present invention relates to the use of piperphentonamine or pharmaceutically acceptable salts thereof to prevent/treat encephalopathy in mammals, and the use of a combination of piperphentonamine or pharmaceutically acceptable salts thereof and other medicines in manufacture a medicine to prevent/treat encephalopathy in mammals. The mammals include human beings, and the encephalopathy includes cerebral injury related diseases or cerebrovascular diseases. The cerebrovascular diseases refer to cerebral ischemia, cerebral ischemia/reperfusion-induced injury or cerebral hemorrhage. The cerebral hemorrhage includes hypertensive cerebral hemorrhage, cerebral hemorrhage secondary to infarction, tumor cerebral hemorrhage or cerebral hemorrhage caused by arteritis. The cerebral ischemia means carotid system cerebral ischemia or vertebrobasilar cerebral ischemia.

10 Claims, No Drawings

USE OF PIPERPHENTONAMINE OR SALTS THEREOF IN MANUFACTURE OF MEDICAMENTS FOR TREATING BRAIN DISEASES

CROSS-REFERENCE TO RELATED APPLICATIONS

This application is the U.S. national phase application of PCT International Application No. PCT/CN2009/074526, filed on Oct. 20, 2009, which claims priority to China Patent Application No. CN200910307637.4, filed on Sep. 24, 2009. The above application(s) is hereby incorporated herein by reference.

SEQUENCE LISTING OR PROGRAM

Not applicable

FIELD OF INVENTION

This invention relates to piperphentonamine or salts thereof and their use of preventing/treating encephalopathy of mammals including human, specifically to their use of preventing/treating cerebral ischemia, ischemia and reperfusion injury, cerebral hemorrhage and cerebral injury.

BACKGROUND OF THE INVENTION

Encephalopathy is a large category of disease with any brain organic injury, cerebral neuron tissue injury caused by heredity, congenital atelencephalia, cerebral trauma, cerebral tumor, cerebral hemorrhage, cerebral infarction, infection, poisoning by chemical drugs, and so on, which cause symptom and physical sign of patients' hypophrenia, thought and language obstacle, sense abnormity, hemiplegia and even incontinence, and so on. Common encephalopathy can be divided into three categories: the first is infantile brain paralysis, hypophrenia etc. caused by genetic, congenital hypogenesis; the second is acute cerebral injury sequela caused by trauma, and cerebral apoplexy sequela caused by cerebrovascular disease, etc; the third is chronic degenerative disease of cerebral neuron aging degradation caused by central nerve fiber injury, including Alzheimer's disease, brain atrophy, Parkinson's disease, etc.

For all sorts of encephalopathy, it is the pathological nature of encephalopathy that results in losing the function of brain neuron, which is the blockage of neural information transmission channel (brain road)—nerve fiber interferes the conduction of diversified nerve information. For example, stroke is a damage, fracture, jam of nerve fiber conduction function, due to cerebral vascular blockage or rupture, which again causes neuron degeneration, injury or death, the emerging hemiplegia, aphasia and other dysfunction of sensory, movement. Another example is that if fetal brain nerve fiber development is blocked, neuronal cell differentiation and maturation cannot be promoted, and newborns is ischemic, hypoxic, resulting in cerebral palsy of central movement dysfunctions mainly. Another example is that Parkinson's disease is caused by decrease of the number of brain substantia neuron, and deficiency of dopamine synthesis; the senescence and apoptosis of the information transmission channels on the nerve fibers are exacerbated, causing the aging of brain cells (brain atrophy) and finally, senile dementia.

Encephalopathy is a more and more serious threat to human health, and also one of the hot issues concerned in present society, medical community. According to the survey, the number of cerebral infarction, cerebral hemorrhage, cerebral atrophy in dementia, infantile cerebral palsy, epilepsy, Parkinson's disease, traumatic brain injury, brain nerve injury diseases account for about 30% of the total number of human disease. And cerebral infarction, cerebral hemorrhage, etc have four-high characters of high incidence, high mortality, high disability rate, high recurrence rate. The annual number of new encephalopathy patients is about 10 million cases in China, the mortality rate is about 75%, the medical expenses on the treatment of encephalopathy in country and family amounts to hundreds of billion Yuan.

Cerebral vascular diseases are divided by arterial injury into: cerebral infarction, cerebral hemorrhage, subarachnoid hemorrhage, hypertensive encephalopathy and other types of arterial diseases. Cerebral vascular disease divided by vein injury is mainly intracranial venous system thrombosis, and the most common is cerebral infarction, cerebral hemorrhage. Cerebral hemorrhage is the intracerebral hemorrhage caused by the rupture of cerebral arterial, venous or capillary, which account for about 20% to 30% of all the cerebral vascular disease.

Stroke also called apoplexy or cerebrovascular accident, is acute localized, transient or permanent brain damage caused by ischemia or hemorrhage, usually including a group of diseases containing cerebral hemorrhage, cerebral infarction, subarachnoid hemorrhage, which is in top 3 reason of human death and the first reason of disabling. According to the Ministry of health survey, annual stroke rate is 150 per 100 thousand, fatality rate is 120 per 100 thousand in China, the existing number of stroke patients is about 5 to 6 million, in which about 75% of the people loss working ability in different degrees, severe disabled people accounts for more than 40%. With the aging of the population, stroke problem will become more serious, society and economy will be overwhelmed. The ischemic stroke accounts for 43%-65% of the acute cerebral vascular disease, the fatality rate is 15%-25%, it is a problem hard to be resolved in our medical community.

At present, more and more domestic and international reports point out the importance of early treatment of ischemic cerebral vascular disease, especially within 3 to 6 hours after onset. The research results of tPA thrombolysis of USA NINDS (within 3 hours after onset) show that the number of patient whose neural function recover to normal increase by 11% compared to the control group, but within 36 hours the intracranial hemorrhage of treatment group is increased significantly (6.4% vs 0.6%). Due to thrombolytic therapy is still in initial research phase with early high hemorrhage rate, the risk/efficacy ratio needs to be defined. Anticoagulant therapy (including heparin and peroral anticoagulants) has been used for preventing from thromboembolism expansion and progressive cerebral vascular disease, transient cerebral ischemic attack, vertebral—basilar artery thrombosis and preventing from cerebral thromboembolism recurrence for a long time, the efficacy remains uncertain, if it is improperly used, the risk of intracranial and systemic hemorrhage is increased. The research reports of large randomized, controlled, double-blind on defibringen treatment is not many, and is still in the research stage. The problems of what extent the defibringen is, how to reduce hemorrhage complications, remain to be solved, and the efficacy has to be further evaluation yet.

In the interventional therapy, according to the report, carotid endarterectomy has made a certain effect for prevention and cure of transient cerebral ischemic attack, the curative effect is good relatively for the patient whose internal carotid artery occlusion is more than 70%. Although these interventional therapy has attracted more and more attention, but information including that of intracranial and extracranial vascular percutaneous transluminal angioplasty intravascular stent implantation or combined with thrombolytic therapy is little, which is still in research stage, lacking of mature experience.

Cerebral protective agent is a hotspot of current research, it has certain basis in theoretic, but from now on, the preparation with determinate effective by clinical study has not found yet.

In conclusion, there has been no big breakthrough in the treatment of acute ischemic cerebrovascular disease from now on. Although there are many methods within which some are still in study stage, but the efficacy is not very sure yet. There is an urgent need to develop a new medicine with good efficiency, little toxic effect, novel chemical structure, capability of treating cerebrovascular disease in clinic, and it is helpful to understand the cerebral vascular disease pathophysiology process deeply.

Craniocerebral trauma is in the second place of incidence rate of systemic trauma, but the mortality and morbidity rank the first. Our Country has about 600000 of traumatic brain injury patients every year, in which about 100000 people died. Craniocerebral trauma has become the most important injury lethal factor of children and young people in developed country. Craniocerebral trauma patients usually present with loss of consciousness, motor nerve dysfunction, memory impairment and mental dysfunction. In order to save the lives of patients, improve their living state, clinicians often use a variety of cerebral protection medicine, hoping to promote the recovery of the patients' brain function. But based on "Chinese craniocerebral trauma patients of cerebral protection medication guide" which is first issued in 2008 by the Chinese Medical Association of neurosurgeons branch, neurological trauma experts committee of China, the clinical curative effect of some common-used drugs is poor, and some drugs are even harmful.

Except the rescue time has to be fast, the more important for treatment of Craniocerebral trauma patients is how to use effective protection drugs rationalized, standardized. The therapeutic levels of craniocerebral trauma are very different between hospitals at present in our country, the therapeutic method is not standardized and rational, it is different in understanding too. Since a long term, there have been a large number of so-called cerebral protection drugs in clinic, it is blindfold to choose and use those drugs. The foreign scholars have adopted evidence-based medicine method, more than 200 categories of brain protection drugs are used in the treatment of acute craniocerebral trauma patients, but failed to find any category of drug with big clinical effects. While some foreign authoritative medical journal, such as "Lancet", "new England medicine", on which the latest research findings are published about those medical drugs is also disappointing: such as, the international multicenter found that a large dose hormone can increase the mortality of patients through more than 10000 cases of evidence-based medicine study; the research reports of 7 medical centers of USA show that magnesium sulfate is ineffective on acute craniocerebral trauma patients, and even harmful; albumin is a drug in common usage in clinical treatment of acute craniocerebral trauma brain edema, but it might be harmful to use for inappropriate long-term and large doses; a large sample research of 35 hospitals in 13 countries found that nimodipine, one of the calcium antagonists, has no therapeutic effect on traumatic subarachnoid subarachnoid hemorrhage.

According to research results above, combined with China's basic national conditions and the actual situation of clinical diagnosis, "therapeutic guidelines of brain protection drugs for China craniocerebral trauma patients" presents opinions about 10 categories of drugs as follows: do not recommend strongly on using a large dose hormone, magnesium and super large amounts of albumin; and use conventional dose according to pharmacopoeia. Do not recommend on using nimodipine, glutamate receptor antagonists, free radical scavengers, bradykinin antagonists and mitochondrial function protection agent. Recommend on using cautiously a variety of peptide brain nerve nutrition drugs, whose curative effect on craniocerebral trauma patients lack the first-class clinical evidence of evidence-based medicine. Recommend on the using ATP, coenzyme A, vitamin B6 and vitamin C, which has no adverse reaction attested by long-term clinical application, and prices are cheaper, pharmacological effects are clear.

Therefore, there is a great need of a new cerebral protective medicine in clinic.

SUMMARY OF THE INVENTION

An object of the present invention is to provide a use of piperphentonamine or salts thereof in manufacture of a medicine for preventing/treating encephalopathy.

The curative effect of the piperphentonamine or pharmaceutically acceptable salts thereof for preventing/treating cerebrovascular disease and cerebral injury is obvious, and of which toxic side reaction is small.

A use of piperphentonamine or pharmaceutically acceptable salts thereof in manufacture of medicine for preventing/treating encephalopathyin in mammal.

Preferably said mammal is human; said medicine is preferably brain protective medicine.

A use of piperphentonamine or pharmaceutically acceptable salts thereof in manufacture of a medicine for preventing/treating encephalopathy in human.

The encephalopathy includes cerebral injury disease or cerebrovascular disease.

The cerebrovascular disease refers to cerebral ischemia, cerebral ischemia/reperfusion injury or cerebral hemorrhage.

The cerebral hemorrhage includes: hypertensive cerebral hemorrhage, cerebral hemorrhage secondary to infarction, tumor cerebral hemorrhage or cerebral hemorrhage caused by arteritis; the cerebral ischemia includes: carotid system cerebral ischemia or vertebrobasilar cerebral ischemia.

A use of piperphentonamine in manufacture a medicine for preventing/treating cerebral ischemia and ischemia/reperfusion injury.

In the present invention, it is shown that piperphentonamine has significant therapeutic effects on cerebral infarction caused by cerebral ischemia and ischemia/reperfusion injury in vivo animal experiments.

The use of piperphentonamine or salts thereof in manufacture a medicine for treating ischemic cerebrovascular disease, wherein the ischemic cerebrovascular disease refers to cerebral infarction, cerebral arteriosclerosis. In the present invention, it is shown by experiments that piperphentonamine and pharmaceutically acceptable salts thereof can decrease vascular permeability, resist lipid peroxidation; and protect the damaged cerebral cells, thus they play a role in the treatment of ischemic cerebrovascular disease.

A pharmaceutical composition consists of said piperphentonamine or pharmaceutically acceptable salts thereof, and a pharmaceutically acceptable carrier and/or diluent.

The pharmaceutically acceptable carrier and/or diluent is well-known by the person skilled in the art, that is to say, the person skilled in the art can obtain the pharmaceutically acceptable carrier and/or diluent through limited experiments according to actual needs. Therefore, the person skilled in the art is not required to pay more creative work.

A use of the pharmaceutical composition combined with other drugs in manufacture a medicine for preventing/treating cerebral injury.

A use of the pharmaceutical composition combined with other drugs in manufacture a medicine for preventing/treating cerebrovascular diseases.

In the invention, it is also observed and studied that the protective effect of piperphentonamine on cerebral hemorrhage model of rat induced by collagenase in three aspects such as neurobiochemistry, neuropathology and behavioral science.

The present invention provides a use of piperphentonamine hydrochloride in protecting mice vascular dementia caused by cerebral ischemia/reperfusion.

In the present invention, it is also shown that the alone or combined use of piperphentonamine has significantly protective effect on cerebral ischemia and cerebral injury in rats in vivo animal experiments.

Wherein the piperphentonamine salts is pharmaceutically acceptable piperphentonamine salts, including organic acid salt, inorganic acid salt, organic alkali salt or inorganic alkali salt, wherein the organic acid includes acetic acid, citric acid, lactic acid, succinic acid, maleic acid, fumaric acid, glucuronic acid, trifluoroacetic acid, Methanesulfonic acid, toluenesulfonatic acid, tartaric acid; the inorganic acid includes hydrochloric acid, hydrobromic acid, nitric acid, sulfuric acid, phosphoric acid; the organic base including ammonium, meglumine, glucosamine, arginine, lysine, ornithine, histidine; the inorganic alkali salts including sodium, potassium, calcium, magnesium, zinc, barium, lithium salt.

The pharmaceutically acceptable salts are preferably piperphentonamine hydrochloride.

The present invention provides a use of piperphentonamine hydrochloride for injection in cerebral protection.

The present invention also provides a method for preventing/treating encephalopathy in mammal, the method comprises administering a drug containing piperphentonamine or pharmaceutically acceptable salts thereof to the subjects.

The mammal refers to human; the encephalopathy refers to cerebral injury disease or cerebrovascular disease; the cerebrovascular disease refers to cerebral ischemia, cerebral ischemia/reperfusion injury or cerebral hemorrhage; the cerebral hemorrhage includes: hypertensive cerebral hemorrhage, cerebral hemorrhage secondary to infarction, tumor cerebral hemorrhage or cerebral hemorrhage caused by arteritis; the cerebral ischemia includes: carotid system cerebral ischemia or vertebrobasilar cerebral ischemia.

The present invention also provides a medicine comprising piperphentonamine or pharmaceutically acceptable salts thereof, the medicine is used for preventing/treating encephalopathy in mammals.

The mammal refers to human; the encephalopathy refers to cerebral injury disease or cerebrovascular disease; the cerebrovascular disease refers to cerebral ischemia, cerebral ischemia/reperfusion injury or cerebral hemorrhage; the cerebral hemorrhage includes: hypertensive cerebral hemorrhage, cerebral hemorrhage secondary to infarction, tumor cerebral hemorrhage or cerebral hemorrhage caused by arteritis; the cerebral ischemia include: carotid system cerebral ischemia or vertebrobasilar cerebral ischemia.

The piperphentonamine is used for preventing/treating cerebral ischemia or ischemia/reperfusion injury.

Piperphentonamine hydrochloride (also known as hydrochloric piperphentonamine) has the following structure:

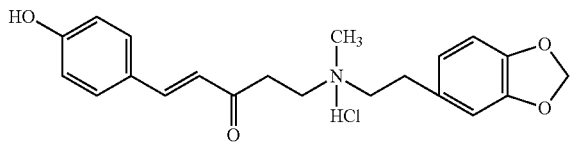

C21H24O4NCl = 389.5

In using, the piperphentonamine and its pharmaceutically acceptable salts of the present invention can be made into water formulation, powder-needle, tablet or capsule etc., using methods of intravenous injection, intramuscular injection or oral administration respectively. According to the different animals and experimental models, a dosage is 0.1 to 80 mg/kg.

The dosage varies with the condition of patients, age and weight of patients. In the case of intravenous injection, the dosage is usually 1 to 4 mg/kg/day for adult; in the case of intramuscular injection, the dosage is usually 2 to 10 mg/kg/day for adult; in the case of oral administration, the dosage is usually 20 to 60 mg/kg/day for adult.

In the present invention, it is shown that the use of piperphentonamine hydrochloride in manufacture a medicine for treating cerebrovascular disease has good therapeutic effects both for cerebral ischemia and cerebral reperfusion injury by pharmacological study. The present invention reveals that piperphentonamine or its salt is a compound with good treatment effect, low toxic side reaction after studying from physiological function, neurons biochemics and pathological morphology, etc, and the curative effect is better than existing drugs for cerebrovascular diseases. Piperphentonamine or its salt is potential to be developed into a new drug for the treatment of cerebral vascular diseases, against cerebral ischemia and reperfusion injury and brain damage.

Furthermore, the synthesis route of piperphentonamine and its pharmaceutically acceptable salts of present invention are rationally designed, the synthesis process is simple, the raw material is available easily, each step of reaction condition is stable, and recovery rate is stable and no serious three waste pollution. Waste reaction solution is acid, alkali solution mostly that can be discharged after simple treatment, which entirely meet with the requirement of industrialized production.

BRIEF DESCRIPTION OF THE DRAWINGS

Not applicable.

DETAILED DESCRIPTION

Embodiments

The following are examples of the invention which are used to describe the invention; however, the present invention is not limited to these examples.

Example 1

The Preventative and Therapeutic Effect of Piperphentonamine and Piperphentonamine Hydrochloride on Cultured Cerebral Neurons Injury 1. Experimental Animal:
Ordinary level Sprague Dawley rats, 18, weight 250 g-280 g. Polymer lysine is from Sigma company; DMEM culture medium is from Gibco; the other reagents are at the analytically pure level.

2. Neurons in Primary Culture

Anesthetizing rats at 15-day of pregnancy by chloral hydrate, disinfecting chest and abdomen by 75% ethanol, taking fetal rat out under aseptic conditions, striping and separating the cortical tissue of both sides, cutting into shape of surimi with operation knife, transferring to the phosphate buffer solution in which contains 0.125% trypsin for digesting for 30 min (37° C.), then discarding the digestive fluid, adding DMED culture solution containing 10% fetal bovine serum, 10% horse serum, 100 U/ml penicillin, and 100 U/ml streptomycin, blowing repeatedly and dispersing with the small caliber straw, filtrating by 200 mesh cells sieve, adjusting the cell concentration to $10^5$/ml with DMEM and inoculating to culture vessel with 2 ml pre-coated with 0.01% polylysine incubating in the $CO_2$ incubator at 37° C., adding cell division inhibitors cylocide stock solution to inhibit the excessive proliferation of non-neuronal cells in the third day of culture, changing the fresh culture medium after taking action for 48 h, then replacing the liquid 2 times a week, and replacing with a half volume of liquid each time.

3. NMDA Induces Neuron Injury

After culturing the cell to 14 day, dividing randomly into normal control group, N-methyl-D-aspartate (NMDA) 50 mmol/L injury group, NMDA+piperphentonamine (JBTA1 50 mmol/L) NMDA+piperphentonamine hydrochloride (JBTA2 10, 100 mmol/L) group, and NMDA+Ganglioside (Ganglioside, GM, 50 mmol/L) control group. In each group, replacing with low serum DMEM with different drugs (fetal bovine serum5%, horse serum5%, HEPES 30 mmol/L) to continue culturing 6 h, adding NMDA 50 mmol/L, then observing the cell morphology, counting 200 cells, and calculating the cell mortality, after incubating 12 h.

4. Results

4.1 The Influence on the Morphological Change of Culture Neuron

When normal neurons are cultured to 14 d, growth is good, the cell body is conical, fusiform or triangle, synapses are long and thick, and forming a root-shape and weaving into a net; when the cells incubate in 50 mmol/L NMDA culture medium for 12 h, the cells is swelled and fuzzy contour, synapses of neurons ruptures and disappears, even the cell is disintegrated; if cell incubate with 10, 100 mmol/L piperphentonamine hydrochloride at the same time, the degree of cell injury reduces significantly, cell morphology remains mainly intact, but cell density decrease, the phenomenon of rupturing of the synapse can still be found; it is shown that piperphentonamine hydrochloride has the significant protective effect on rat neuron injury induced by NMDA. The protection function of ganglioside 50 mmol/L is equal to the one of piperphentonamine hydrochloride 10 mmol/L.

4.2 The Influence on Mortality of Cultured Neuron

After neurons are incubated in 50 mmol/L NMDA culture medium for 12 h, trypan blue stained cells significantly increase (NMDA group 55% vs normal controls group 10%, P<0.001), which indicates cell mortality increasing; adding 10, 100 mmol/L piperphentonamine hydrochloride to the medium (38%, 24% respectively) can reduce cell mortality significantly, and difference is significant compared with NMDA group.

TABLE 1 the influence on mortality of cultured neuron

| Grouped | doses (mmol/L) | mortality |
|---|---|---|
| Normal control | — | 10% |
| NMDA | 50 | 55% |
| NMDA + JBTA$_1$ | 50 | 30% |
| NMDA + JBTA$_2$ | 10 | 38% |
|  | 100 | 24% |
| NMDA + GM | 50 | 40% |

Example 2

Therapeutic Effect of Piperphentonamine and Piperphentonamine Hydrochloride on Closed Traumatic Cerebral Injury of Mice Automatic recorder of diving platform experiment is from electric instrument room of Chinese Academy of Medical Sciences Medicine Institute; fluorescence spectrophotometer is from Japanese company HITACHI; Microplate reader.

Experimental animal: clean Kunming mice, weight 20 g-22 g.

Seventy mice were divided randomly into seven groups: Control group, model group, 2 mg/kg piperphentonamine (dilute to a suitable concentration with 5% glucose injection for use, hereinafter similarly) group, piperphentonamine hydrochloride 1 mg/kg group, 2 mg/kg group, 4 mg/kg group and ATP 4 mg/kg group. There were 10 mice in each group.

The closed cerebral trauma model of mice being established after fasting for 16 hours, administering intravenously to each group, striping and taking the brain of mouse after 24 hours, weighing the wet weight, and drying at 70° C. for 24 hours, then weighing the dry weight, and calculating brain-water content; the brain water content which is higher than normal values indicates the cerebral edema.

The results being shown in Table 2, closed cerebral trauma induce serious edema of the mouse brain. After administering different doses of piperphentonamine hydrochloride or piperphentonamine, cerebral edema of mice has decreased in different degrees, which depends on dosage. The effect of piperphentonamine is better than the one of ATP.

TABLE 2 the influence of piperphentonamine on cerebral edema of mice caused by closed cerebral trauma (x ± SD, n = 10)

| Experiment group |  | water content of cerebra (%) |
|---|---|---|
| normal control group |  | 75.15 ± 6.29** |
| model group |  | 89 ± 9.24 |
| piperphentonamine | 2 mg/kg | 78.31 ± 5.72** |
| piperphentonamine hydrochloride | 1 mg/kg | 82.05 ± 7.57* |
|  | 2 mg/kg | 78.67 ± 5.38** |
|  | 4 mg/kg | 75.43 ± 8.38** |
| ATP | 4 mg/kg | 79.15 ± 6.83* |

Comparing with the model group,
*P < 0.05,
**P < 0.01

Example 3

Preventive and Therapeutic Effect of Piperphentonamine Hydrochloride on the Mouse Nerve of Vascular Dementia Piperphentonamine Hydrochloride was diluted to a suitable concentration with 5% glucose injection for use. Automatic recorder of Diving platform experiment is from electric instrument room of Chinese Academy of Medical Sciences Medicine Institute; fluorescence spectrophotometer is from Japanese company HITACHI; Microplate reader.

Experimental animal: clean Kunming mice, weight 20 g-22 g.

1. The Improving Effect of Piperphentonamine Hydrochloride on Mice Learning and Memory Dysfunction Caused by Cerebral Ischemia Reperfusion.

The animals were randomly divided into five groups: sham operation group, model group, piperphentonamine hydrochloride 1 mg/kg group, 2 mg/kg group, 4 mg/kg group. There were 10 mice in each group.

After the mice were fasted for 16 hours, we established the dementia model of mice caused by ischemia reperfusion. The preparatory steps were proceeded as follows: anesthetizing mouse by sodium pentobarbital (60 mg/kg, ip), supinely immobilizing on a board, incising on the midmost of neck, isolating bilateral common carotid artery, and threading with zero-size silk thread. Afterwards, operation steps were proceeded as follows: blocking the blood flow of bilateral common carotid artery for 10 min, then resuming the blood flow for 10 min, repeating the blocking/resuming steps for 3 times, and suturing the skin. The mice were put in normal feeding conditions. Bilateral common carotid artery is only isolated for sham operation group.

After ischemia reperfusion for 10 min, the drugs are injected on tail vein, after ischemia reperfusion for 24 h, administering for the second time. Carrying on the platform-diving experiment after administering for half an hour. The mice under test are put into the platform-diving instrument, adapting the environment for 3 min, and then the bottom plate being electrified, observing the time when the mouse jump onto the high platform (reaction time) and the times which the mouse jump down from the high platform and are shocked by electricity in 5 min (the number of errors in the training period). After 24 h, administering again, then carry on the second platform-diving experiment to measure the function of obtaining memory. Putting the mouse on the platform of experimental instrument, electrifying the bottom plate at the same time, recording the time when the mouse jump down from the high platform (latency) and the times which shock by electricity in 5 min (the times of error in test-retest period).

The results being showed in Table 3, repeated cerebral ischemia reperfusion can make mice exhibit a marked obstacle of learning and memory, the reaction time prolong, the error times increase, and the latency shorten. Piperphentonamine hydrochloride has a improved effect on learning and memory obstacle induced by ischemia reperfusion, reduces the reaction time, prolongs the latency period, and reduces the error times of the test time and test retest period, it is significantly different compared with the model group ($P<0.05$ or $**P<0.01$).

TABLE 3 the influence of piperphentonamine hydrochloride on the function of learning and memory of cerebral ischemia reperfusion in mice (x ± SD, n = 10)

| Group | Learning achievement | | memory achievement | |
|---|---|---|---|---|
| | Reaction time s | Error times | latency s | Error times |
| sham operation group | 10.44 ± 7.98** | 4.21 ± 2.18** | 357.86 ± 128.5** | 0.44 ± 1.45** |
| model group | 34.95 ± 22.19 | 11.89 ± 5.08 | 133.69 ± 128.62 | 3.63 ± 2.32 |
| piperphentonamine hydrochloride | | | | |
| 1 mg/kg | 16.53 ± 11.75* | 5.37 ± 3.63* | 249.84 ± 133.55* | 1.31 ± 0.58* |
| 2 mg/kg | 13.34 ± 8.85* | 5.08 ± 3.34** | 308.13 ± 97.73** | 0.73 ± 0.58** |
| 4 mg/kg | 7.11 ± 4.06** | 4.5 ± 3.05** | 352.79 ± 141.5** | 0.58 ± 1.45** |

Compared with model group,
*P < 0.05,
**P < 0.01

2. The Influence of Hydrochloric Acid Piperphentonamine on Sod Activity, Content of MDA and GSH in Cerebral Ischemia Reperfusion of Mouse Cerebra Ischemia reperfusion method in the mouse and the administration method are the same as above. After ischemia reperfusion is completed, executing by decollating, removing the brain and making homogenate by phosphate buffer in 0° C., determining the activity of SOD by pyrogallol autoxidation method, the content of MDA by TBA method, and the content of GSH by DTNB method, quantitate the protein by Coomassie brilliant blue method.

The results are shown in Table 4, the repeated cerebral ischemia reperfusion can make SOD activity of mouse cerebral homogenate decrease, content of MDA increase, and content of GSH decrease. Administering different doses of piperphentonamine hydrochloride can inhibit the elevation of MDA of is brain tissue of chemia-reperfusion in mouse, increase the content of GSH, increase the activity of SOD, it is significantly different compared with the model group ($P<0.05$ or $P<0.01$).

TABLE 4 the influence of piperphentonamine hydrochloride on SOD, MDA and GSH of ischemia reperfusion injury of mouse brain (x ± SD, n = 10)

| group | SOD Ku/g pr | MDA nmol/g pr | GSH mg/g pr |
|---|---|---|---|
| sham operation group | 0.53 ± 0.04** | 3.23 ± 0.68** | 18.8 ± 5.84** |
| model group | 0.25 ± 0.04 | 5.3 ± 0.94 | 5.86 ± 1.96 |
| hydrochloric acid | | | |

TABLE 4-continued the influence of piperphentonamine hydrochloride on
SOD, MDA and GSH of ischemia reperfusion injury of mouse
brain (x ± SD, n = 10)

| group | SOD Ku/g pr | MDA nmol/g pr | GSH mg/g pr |
|---|---|---|---|
| piperphentonamine | | | |
| 20 mg/kg | 0.34 ± 0.02* | 4.48 ± 1.03* | 10.34 ± 3.17* |
| 40 mg/kg | 0.37 ± 0.02** | 3.74 ± 0.67** | 13.1 ± 4.34** |
| 80 mg/kg | 0.42 ± 0.04** | 3.53 ± 0.76** | 14.77 ± 4.61** |

Compared with model group
*P < 0.05,
**P < 0.01

Example 4

The Embodiment Relates to the Experiment In Vivo of Piperphentonamine Hydrochloride for Preventing Infective Cerebral Edema SD rats has 30, and weight is about 210 g. Dividing into 3 groups randomly: physiological saline control group (NS, n=10); pertussis Bacteria liquid model group (PB, n=10); pertussis Bacteria liquid pretreated by piperphentonamine hydrochloride group (JBTA, n=10).

Cutting in the midmost of neck of rat, separating common carotid artery of the left neck, external carotid artery, internal carotid artery and its branches, and ligating pterygopalatine artery and the occipital artery. After clipping the external carotid artery, the pertussis bacteria liquid 0.2 ml/kg (pertussis bacteria liquid is inactivated bacteria liquid provided by Beijing Institute of biological products with bacteria content 10.8×109/ml) is injected to the left internal carotid artery by puncturing the left common carotid artery by using 1 ml injector with 4.5 needles, and completing injection within 15 s. NS group is inject with the equal volume of physiological saline with same method. Before 48 h on injecting pertussis bacteria liquid, the hydrochloric acid piperphentonamine group is intravenously injected 0.5 mg/kg daily on consecutive two days. The rats in each group are injected bacteria or saline for 4 h, then executed by decollating.

Determine the content of IL-1β, TNF-α and NO by using ELISA and Griess method.

Pretreated by piperphentonamine hydrochloride, the content of water and the content of sodium ion decrease prominently in cerebral edema of rats of pertussis Bacteria liquid, and the content of potassium ion increase. It shows that the pretreatment of piperphentonamine hydrochloride has protective effect on the infective brain edema of rats. The results are shown in Table 5.

TABLE 5 the change of water and sodium potassium ion content of brain
after the pretreated by piperphentonamine hydrochloride

| groups | Animal number | water content of brain (%) | Na+(nmol/kg) | K+(nmol/kg) |
|---|---|---|---|---|
| NS | 10 | 69.2 ± 0.26 | 170.9 ± 6.25 | 393.1 ± 9.77 |
| PB | 10 | 72.3 ± 0.26[1] | 243.8 ± 16.3[1] | 315.3 ± 22.0[1] |
| JBTA | 10 | 69.8 ± 0.44[3] | 181.1 ± 26.1[3] | 436.3 ± 43.9[1)2] | notes:
compared with NS [1]P < 0.01
compared with NS [2]P < 0.05
compared with PB [3]P < 0.01

The content of IL-1β, TNF-α and NO of pretreatment of piperphentonamine hydrochloride group prominently decrease (P<0.01), The results are shown in Table 6.

TABLE 6 the influence of the pretreatment of piperphentonamine
hydrochloride on the content of IL-1β, TNF-α
and NO in rat cerebral tissue of infective brain edema

| groups | IL-1β(pg/g) | TNF-α(pg/g) | NO(nmol/g) |
|---|---|---|---|
| NS | 254.1 ± 70.4 | 350.7 ± 80.3 | 76.55 ± 8.40 |
| PB | 403.3 ± 39.5[1] | 800.3 ± 89.1[1] | 111.3 ± 14.4[1] |
| JBTA | 318.4 ± 43.8[2)3] | 499.7 ± 134.9[2)3] | 86.1 ± 5.9[2)3] | notes:
compared with NS [1]P < 0.01,
compared with NS [2]P < 0.05,
compared with PB [3]P < 0.01

The brain water content, sodium ion content of rats increase, and potassium ion content decrease, after the injection of bacteria liquid for 4 h, which reveals that the model of infective brain edema is established. At the same time, the content of IL-1β, TNF-α and NO in rat cerebral tissue increase, it has very prominent difference compared with the corresponding NS control group (P<0.01). It hints that they have a close connection with infective brain edema, and the great generation of those factors can aggravate the infective cerebral injury. The invention find out that the content of IL-1β, TNF-α and NO in cerebral tissue prominently decrease in the infective cerebral edema model of rats established after the pretreatment of piperphentonamine hydrochloride, compared with the infective cerebral edema model of rats without pretreatment, At the same time, the brain water content, sodium ion content decrease, the potassium ion content increase, and it is very prominent different compared with model groups (P<0.01). It is shown that piperphentonamine hydrochloride have protective effect on infective cerebral edema of rats by decreasing the generation amount of IL-1β, TNF-α and NO.

Example 5

This embodiment relates to experiment in vivo of piperphentonamine hydrochloride combined the medication which is commonly used in clinic for the encephalopathy for preventing and treating infectious cerebral edema.

The model of infectious cerebral edema is same with example 4. It is Studied that piperphentonamine hydrochloride and a blocker for specificity L-type calcium ion channel nimodipine influence on the brain water content and Evans blue (EB) content of infectious cerebral edema, of which the purpose is to provide experimental and theoretical basis for clinical treatment.

Ninety healthy SD rats are divided into 4 groups randomly, namely, (1) physiological saline control group (NS), 20; (2) pertussis bacteria liquid group (PB), 30; (3) nimodipine treatment group (Nim), 20; (4) nimodipine treatment group after being pretreated by piperphentonamine hydrochloride (JBTA+Nim), 20. Each group is further divided into three time group such as 30 min, 4 h and 24 h group.

Injecting intravenously nimodipine after injecting bacteria for 5 min (Nim group, body weight 0.25 mg/kg), 24 h nimodipine treatment group is repeatedly injected the same dose once per 8 h; nimodipine treatment group pretreated by piperphentonamine hydrochloride is intravenously infused piperphentonamine hydrochloride (0.5 mg/kg, 2 times in total) before experimenting for 48 h and 24 h, then treated with nimodipine after the pretreatment. The operation of physiological saline group being same as bacteria liquid group, is injected the same volume of physiological saline at the same time. 2% Evans blue (EB, 0.2 mL/100 g body weight) is injected from the vein of the sublingua after injecting bacteria or saline in 10 min. Each group of animal is executed by decollating after observing to the specified time, rapidly removed the brain, and remove the leptomeninges and coagulation block of the cortical surface, taking full-thickness brain tissue of the back ⅓ of left hemisphere of the brain (about 0.1~0.2 g, including gray matter and white matter) as specimens, the water content in brain tissue and the Evans blue content are determined by the dry wet method, and brain tissue is examined by electron microscope.

The mean, standard deviation, analysis of variance and correlation analysis of the water content and EB content of the brain tissue in the time groups of infectious cerebral edema are shown in the following table. The results is shown that, the water content and EB content of the brain tissue injected bacteria after treated by nimodipine is obviously lower than that of pertussis Bacteria liquid group (P<0.05), and the effect of 4-hours treatment group is the best. The water content and EB content of the brain tissue in nimodipine treatment group after being pretreated by piperphentonamine hydrochloride do not significantly change in 30 min time group, and it is significantly lower in 4, and 24 h group (P<0.05), is significant difference with alone nimodipine treatment groups (P<0.01). The water content of brain and EB content of each sub time group of Bacteria liquid group has high positive correlation (r<0.90, P<0.05).

TABLE 7

EB and brain water content (BWC) and the correlation coefficient of infectious cerebral edema of rats in different time (x ± SD)

| | | n | BWC(%) | EB(μg/g ww) | r(P) |
|---|---|---|---|---|---|
| 30 min | NS | 5 | 76.83 ± 0.39 | 1.5 ± 0.35 | 0.87 (P < 0.05) |
| | PB | 5 | 78.54 ± 0.50$^\Delta$ | 3.01 ± 0.72$^\Delta$ | 0.98 (P < 0.01) |
| | Nim | 5 | 77.26 ± 0.34* | 2.0 ± 0.18* | 0.95 (P < 0.01) |
| | JBTA + Nim | 5 | 76.47 ± 0.64$^\Delta$ | 1.85 ± 0.53$^\Delta$ | 0.97 (P < 0.01) |
| 4 h | NS | 8 | 77.14 ± 0.20 | 1.87 ± 0.37 | 0.98 (P < 0.01) |
| | PB | 10 | 80.24 ± 1.70$^{\Delta\Delta}$ | 5.35 ± 1.78$^{\Delta\Delta}$ | 0.97 (P < 0.01) |
| | Nim | 8 | 77.15 ± 0.66* | 2.65 ± 0.44* | 0.75 (P < 0.05) |
| | JBTA + Nim | 6 | 75.54 ± 0.44* | 1.98 ± 0.70** | 0.96 (P < 0.01) |
| 24 h | NS | 6 | 76.84 ± 0.19 | 1.68 ± 0.41 | 0.99 (P < 0.01) |
| | PB | 10 | 79.23 ± 1.04$^\Delta$ | 3.1 ± 0.9$^\Delta$ | 0.91 (P < 0.01) |
| | Nim | 7 | 76.98 ± 0.50* | 2.00 ± 0.6* | 0.66 (P > 0.05) |
| | JBTA + Nim | 7 | 73.99 ± 0.67* | 1.81 ± 0.77* | 0.54 (P > 0.05) |

*P < 0.05,
**P < 0.01, vs PB group;
$^\Delta$P < 0.05,
$^{\Delta\Delta}$P < 0.01, vs NS group;
BWC = brain water content;
EB = Evan blues;
PB = Pertussis Bacilli The results of electron microscopic examination shows that: the endothelial cell of 4 h bacteria liquid group being obviously swell, the gap of peripheral of cerebral vascular being wide, glial cell foot being markedly swell; cytoplasmic structure being fuzzy, mitochondrion being edema, and organelles being swell. In addition to the above changes, the main representation of 24 h bacteria liquid group is increased uptake and pyknosis of the neuronal nuclei and "dark cells" is appeared, which proves that neurona is in delayed necrosis in 24 h bacteria liquid group Nimodipine is a dihydropyridine category with strongly selective organic calcium antagonist, being prone to penetrate the blood brain barrier (BBB) easily. On one side, it selective effects on cerebral vessels, and having a selective expansion effect on cerebral vessels, and relieving cerebral vasospasm and improving brain microcirculation and protecting BBB; on the other side, nimodipine specifically blocks the L-type calcium channel on neuron membrane, recovering the activity of Ca2+-ATP enzyme, reducing Ca2+ internal flow in cerebral injury, thereby the cerebral edema is relieved. This study found that the water content and EB content of the brain tissue in 4 h and 24 h nimodipine treatment group after being pretreated by piperphentonamine hydrochloride obviously decreased, and the effect is better than the one of the alone nimodipine group. It proves that nimodipine treatment group after being pretreated by piperphentonamine hydrochloride has a preventive role on delayed cerebral edema, namely, the combined applications of L-type calcium channel blockers (such as nimodipine) with piperphentonamine hydrochloride can block the Ca2+ internal flow in extracellular from different links, and having therapeutic effect on infectious brain edema induced by pertussis bacteria liquid of rats.

Example 6

The Therapeutic and Protective Effects of Piperphentonamine Hydrochloride on Local Cerebral Ischemia of Rats Nimodipine Injection is a product of Shandong Xinhua Pharmaceutical Company Limited, specifications: 10 mg/50 ml, TUNEL Kit: Nanjing Jiancheng biological engineering development company.

Experimental animal: 60 general level of SD rats, weigh t 250 g-280 g

1. The Preparation for Local Cerebral Ischemia Model

The animals are randomly divided into sham operation group, model group, nimodipine group (Nim, 1 mg/kg), hydrochloric acid piperphentonamine hydrochloride group (0.5, 1, 2 mg/kg), 10 rats in each group. After fasting for 16 hours, anesthetizing by chloral hydrate (350 mg/kg, IP), separating the right common carotid artery, clip the internal carotid and carotid artery, ligating the proximal end and distal end of external carotid artery, and cutting intermediately. Pulling the free end of the external carotid artery to the internal carotid artery in a straight line, inserting the thread (nylon line of diameter of 0.24, length of 5.0 cm) into the intracranial from the external carotid artery, stopping when meeting with slight resistance, the depth of insertion being about 2 cm. Ligating the openings of external carotid artery, and opening the common carotid artery clamp, disinfecting the suture wounds, the ischemia model (MACO) of local artery in the right cerebra is accomplished; in sham operation group, only separating the right common carotid artery, internal carotid artery, external carotid artery (the above experiments is completed at 23 to 25). The animals of each group are given corresponding drug in 30 min after the operation is complete.

2. Neurobehavioral Score and Determination of Infarction Area by TTC Staining

Observing and recording the behavior disorder of rat After 24 hours: (1) raising the rat tail to observe the forelimb flexion, counting as 0 points if double forelimb symmetrically extend toward the ground, counting as 1 point if the forelimb contralateral to the operation side appears wrist flexion, counting as 2 points if elbow flexion is appeared, counting as 3 points if shoulder internal rotation is appeared, and counting as 4 points if both the wrist flexion and/or bend the elbow, and shoulder internal rotation are appeared. (2) placing the animals in the flat ground, pushing the shoulders to move to contralateral respectively, checking the resistance. Counting as 0 point if bilateral resistance is equal and strong, counting as 1, 2 and 3 points respectively if the one with resistance decline is divided into three degrees of light, medium, heavy according to different degrees of decline when pulling to the contralateral to operation side. (3) putting the double forelimbs of the animal onto a metal net, observing muscle tension of the double forelimbs. It is counted as 0 points if muscle tension of the double forelimbs is equal and powerful. Also it is counted as 1, 2 and 3 points according to the different declined degrees of the tension of muscle contralateral to the operation. (4) it is counted as 1 point if the animal keeps making in circles along one side. According to the score standard, the highest score is 11 points, the higher the scores, the more serious of the animal behavior disorders.

The rats are executed after behavioral score, being taken the brain out, being removed olfactory bulb, cerebellum and the lower brainstem, being cut the coronary slice to 5 pieces, and brain slices are stained by red tetrazolium (TTC), the normal tissue being red after dyed, infarct tissue being white, taking photos after dyed, then calculating the infarction area ratio with pathology image analysis software of China University of Aeronautics and Astronautics.

The results being showed in Table 8, in 24 hours after ischemia, rats show a significant behavioral disorders, obvious focal ischemia necrosis area being appeared in rat brain tissue, which accounts for about 25% of the whole brain; administrated different doses of piperphentonamine hydrochloride (0.5, 1, 2 mg/kg), animal behavior disorders is eased in varying degrees, and the cerebral ischemia area of rats markedly reduce.

TABLE 8 the influence of piperphentonamine hydrochloride on rat neural behavior, cerebral infarction area of local cerebral ischemia ($x \pm SD$, $n = 10$)

| group | Behavior disorder (points) | Ischemia arae (mm$^2$) |
| --- | --- | --- |
| sham operation group | 0 | 0 |
| model group | 10.58 ± 1.27 | 27.26 ± 3.22 |
| nimodipine group | 6.21 ± 2.88** | 21.39 ± 3.45** |
| piperphentonamine hydrochloride group | | |
| 0.5 mg/kg | 7.59 ± 2.19* | 21.51 ± 7.94* |
| 1.0 mg/kg | 6.79 ± 2.65** | 18.17 ± 3.91** |
| 2.0 mg/kg | 4.83 ± 2.53** | 13.57 ± 3.68** |

Compared to model group
*$P < 0.05$,
**$P < 0.01$

Pathological observation: putting the brain slices in 10% formalin to fix after stained by TTC, 8 μm in the thickness of the tissue slices is made after the steps of dehydration, immersing in paraffin, embedding, sectioning, etc, being stained by toluidine blue, and detecting under an optical microscope and counting the number of cell. The Method of counting is following: selecting the pathological slice at the midpoint of the connection line of optic chiasma with infundibular stalk of each rat, calculating the percentage of number of necrotic neuron account for the number of total neuron by using cell counter, with the subcortical basal ganglia of fixed range for the observation object, the necrotic neurons with missing nucleus and dark stained cytosome for the counting object.

The Data is represented by X±SD, use reference difference method (ANOVA) to carry on statistical processing before and after the administration in group and between groups.

The pathological examination results is following: 24 h after MCAO, being pale, dull in blood-supply area of side experimental hemisphere MCA of rats in model group, the pathological slice of brain being shown that, being a necrosis in central area with severe injury and a penumbra area with mild moderate injury and the peripheral area thereof in the cerebral tissue of MCA obstruction side, wherein the penumbra area is sensitive to ischemic changes, in the model group rats, it being shown that the peripheral gap of many neurons enlarges, dark stained neurons is appear sporadically, and neurons is crimple in different levels. Contralateral cerebral tissues show no pathological changes. Animals administrated piperphentonamine hydrochloride treatment group ease in different degrees. The number of cell is counted by the penumbra area of brain slice of the same section. It is shown in Table 9, the necrosis percentage of neurons in cortical, striatum in piperphentonamine hydrochloride treatment group significantly reduces, and it is significantly different compared with model group ($P<0.05$ or $P<0.01$).

TABLE 9 the influence of piperphentonamine hydrochloride on the necrotic percentage of neuron of local cerebral ischemia in rat ($x \pm SD$, $n = 10$)

| | percentage of necrotic neuron (%) | |
| --- | --- | --- |
| Groups | cortical neurons | striatum neurons |
| Sham operation group | 0 | 0 |
| model group | 37.4 ± 11.05 | 27.2 ± 5.1 |
| Nimodipine group | 24.65 ± 4.25* | 17.85 ± 4.25* |
| piperphentonamine hydrochloride | | |
| 0.5 mg/kg | 25.5 ± 3.4* | 18.7 ± 3.4* |
| 1.0 mg/kg | 14.45 ± 2.55** | 12.75 ± 2.55** |
| 2.0 mg/kg | 11.05 ± 1.7** | 9.35 ± 1.7** |

Compare with the model group
*$P < 0.05$,
**$P < 0.01$

Example 7

The embodiment relates to an animal experiment of piperphentonamine hydrochloride using for the preventing cerebral ischemia reperfusion injury disease.

Focal cerebral ischemia reperfusion injury model is made in mice by using suture method, being ischemia for 2 h, then reperfusing for 24 h, and it proves that piperphentonamine hydrochloride has protective effect on ischemia-reperfusion cerebral injury.

Mouse is anesthetized by injecting 10% chloral hydrate (350 mg/kg) in intraperitoneal, being intravenously administered 1 mg/kg, 5 mg/kg piperphentonamine hydrochloride or 20 u/kg coenzyme A, (COA), making the cerebral artery ischemia like as the method of example 6. Pulling out nylon thread from the internal carotid artery after the operation in 2 hours, until the end of the nylon thread is at bifurcation of the common carotid artery. Reperfusing for 24 hours. Except for not inserting a thread, the rest of steps for the false operation group are same as the above-mentioned. After reperfusion for 24 h, decapitating and taking the brain of survived mice, rapidly putting in −20° C. freezer for 5 min, then removing, quickly cutting coronal slices of 2.0 mm thickness from forward to back on the operating table, putting the slices in phosphate buffer solution with 1% TTC immediately, incubating for 30 min in avoiding light at room temperature. Flip brain slices to make them touch staining solution uniformly every 10 minute, and scanning and observing the dyeing results.

Observing the volume of cerebral infarction: because TTC is a liposoluble light-sensitive compound, and a proton acceptor of enzyme system with pyridine-nucleoside structure in respiratory chain, and turning red after reacting with dehydrogenase in normal tissue, and the dehydrogenase activity decreasing in ischemic tissue, not available to react, it is pale without changes. Therefore, the cerebra tissue of sham operation group (A) has no infarction, the side cerebra tissue in ischemia of operation group (B) having obvious phenomenon of brain infarction, the infarction area in cerebra slice occupying 26.7±2.2 percentage (%) of the entire coronal plane. The infarction area in side brain tissue of ischemic prominently reducing in piperphentonamine hydrochloride treatment group (C), and being significant different compared to the operation groups (P<0.01), and the effect of 5 mg/kg piperphentonamine hydrochloride treatment group is better than the one of CoA group.

TABLE 10 the influence of the piperphentonamine hydrochloride on the infarction area in cerebra ischemic model of mouse

| groups | n | The percentage of infarction area occupied the entire coronal plane (%) |
|---|---|---|
| sham operation group (A) | 8 | 0 |
| Ischemia - reperfusion group (B) | 8 | 26.70 ± 2.21 |
| Medicine group (C) | | |
| 1 mg/kg | 8 | 19.78 ± 2.61** |
| 5 mg/kg | 8 | 16.55 ± 2.32** |
| CoA group (D) | | |
| 20 U/kg | 8 | 20.53 ± 4.82* |

Compare with the operation group:
**P < 0.01

The results show that piperphentonamine Hydrochloride has significant protective effect on cerebral infarction induced by cerebral ischemia/reperfusion injury in mice.

Example 8

The Protective of Piperphentonamine Hydrochloride Affects on the Prevention Cerebral Hemorrhage in Rats Experimental animals: male Wistar rats, male and female in half, weight 180 to 250 g, fast 12 h before operation, drink water freely.

1. Experimental Animals Groups

Animals are randomly divided into five groups: sham operation 24 h group; cerebral hemorrhage (Intracerebral Haemorrhage, ICH)+physiological saline group (model); ICH+piperphentonamine hydrochloride (JBTA, 2 mg/kg) group, called as high dose group (h); ICH+piperphentonamine hydrochloride (JBTA, 0.5 mg/kg) group, called as low dose group (l); ICH+nimodipine (Nim, 0.5 mg/kg) group. The last four groups are divided into 4 h, 8 h, 12 h, 24 h as four time subgroups respectively. Physiological saline solution, piperphentonamine hydrochloride and nimodipine are intravenously injected from rat tail before the ICH model is established for 30 minutes, once a day. Injecting slowly, the total amount of drug liquid is controlled in 1 ml/200 g body weight: physiological saline solution also being administered in 1 ml/200 g body weight. Each group has 7 Wistar rats.

2. The Establishment of ICH Rat Model

This article refers to the method reported by Rosenberg, etc. The rat cerebral hemorrhage model in present invention is a model induced by collagenase, the model is one of the most commonly used model of cerebral hemorrhage currently at home and abroad. The collagenase adopted in the model is a metalloproteinase, which is able to degrade collagen of mesenchyme and basement membrane, and being able to degrade the collagen of vascular wall when injecting into the brain, thus, result in bleeding. The model is very close to the clinic in some aspects of pathology such as brain edema, histology and ethology etc., and liquid volume injected into the brain of the model is few, and it almost has no extrusion occupied effect of drug liquid itself.

The specific steps are as following: after the experimental rats are anesthetized by injecting chloral hydrate (350 mg/kg) in intraperitoneal, and being supinely immobilized in a stereotaxic instrument, and make the rat anterior fontanelle and posterior fontanelle in the same plane according to localization method reported by BAO Xinmin, etc. Being locally disinfected by iodine, incising in the midmost of scalp, scissoring the periosteum, exposing the anterior fontanelle, drilling a 1 mm diameter hole with thickness close to duramater in 3 mm left to the midline by number five needle. Inserting needle along the hole by the micro syringe fixed on a stereotaxic, the depth of needle insertion is 5.8 mm (i.e., the caudate nucleus position), slowly injecting collagenase VI 0.5 U. Injection time is 3 min, keeping for 5 min after injection, then pull the needle out, suturing the skin, and putting the rat into cage and feed. Inserting the needle and not injecting drugs in sham operation group, the remaining operations is the same as the above.

Statistical processing: every group measured values are presented by mean+SD (x±SD), carrying on single factor analysis of variance (one-way ANOVA) by using SPSS statistics software, significant level P<0.05.

3. Observational Index and Results 3.1 Neurology Score of ICH Rats

After animals wake up, scoring nerve function defect of each group immediately according to the grading classification standards of nerve defect reported by Bedersog (litter improved).

TABLE 11 the rat neurology score standard of IHC model

| classification | symptom | scores |
|---|---|---|
| 0 | without any symptoms or only the ipsilateral palpebral fissure narrow | 0 |
| I | When lifting tail, the contralateral limb is flexural flexion adducted | 1 |
| II | Resistance to lateral thrust diminish and with grade I symptoms | 2 |
| III | circle towards contralaterally when crawling and with grade II symptoms | 3 |
| IV | loss the consciousness and be not able to walk | |

Choosing the animals with the score of 3 and more into the experiment, the animals are bred in different cages, eat and drink normally. Temperature is controlled in 20 to 25° C., score in 4 h, 8 h, 12 h, 24 h after establishment of the model.

Results: the nerve function defect scores of sham operation group are 0 points at each time point; the scores is 3 or 4 points by scoring the animals of model group immediately after anesthesia, on one hand, it reveals that the establishment of ICH rat model is successful, on the other hand, it reveals that ICH results in a very obvious defect of rat neural function. At the same time, it is observed that the neural function score of each group of ICH rat decrease gradually with time, and the score of drug administered group decrease faster than the one of model group. The score ratio of nerve defect score of large dose of piperphentonamine hydrochloride administration group in 12 h, 24 h after ICH to model group is significant difference from the one of small dose of piperphentonamine hydrochloride groups at the corresponding time point (P<0.05). At 12 h, 24 h after ICH, the score ratio of the nerve defect of nimodipine group to model group has significant difference at the corresponding point time (P<0.05). The above observations show that the nerve defect score after ICH can be improved by intravenously administrating piperphentonamine hydrochloride in 2 mg/kg, of which the effect is better than the one of 0.5 mg/kg nimodipine.

Results: it is found by analyzing table 13, the rats brain water content at 4 h, 8 h, 12 h, 24 h time point after cerebral hemorrhage increase obviously compared with operation group, and it has significant difference (P<0.05), and brain water content increase incessantly with the time progressing, and achieve a peak in 24 hours after cerebral hemorrhage. The brain water content of ICH rat in treatment group decrease in different degree compared with the model groups at each time point. These results show, the administration of piperphentonamine hydrochloride 2 mg/kg can reduce the severity degree of rat cerebral edema after ICH, the therapeutic effect is similar with nimodipine 0.5 mg/kg.

TABLE 12 the influence of piperphentonamine hydrochloride on neurological scores in 4 h, 8 h, 12 h, 24 h after cerebra hemorrhage in rats (x ± SD, n = 7)

| Experiment group | neurological score | | | |
|---|---|---|---|---|
|  | 4 h | 8 h | 12 h | 24 h |
| Sham | 0 | 0 | 0 | 0 |
| ICH | 4.71 ± 1.04 | 129 ± 1.04 | 4.07 ± 1.43 | 3.44 ± 1.14 |
| ICH + JBTA (2 mg/kg) | 4.07 ± 0.74 | 3.86 ± 1.19 | 2.36 ± 0.8*$^\Delta$ | 1.71 ± 0.57**$^\Delta$ |
| (0.5 mg/kg) | 4.5 ± 0.87 | 4.29 ± 1.02 | 3.65 ± 1.19 | 3.21 ± 1.61 |
| ICH + Nim (0.5 mg/kg) | 4.5 ± 0.87 | 4.07 ± 1.14 | 2.57 ± 1.14* | 1.94 ± 0.74** | notes:
*P < 0.05,
**P < 0.01 VS model;
$^\Delta$p < 0.05 VS Nim

3.2 Brain Water Content (BWC) Measurement

Observing the influence of piperphentonamine hydrochloride on the brain water content of intracerebral hemorrhage in rats in 4 h, 8 h, 12 h, 24 h, the animals of the different groups is anesthetized by chloral hydrate at predetermined time point, and decollating and taking the brain rapidly, putting the brain tissue on a filter paper wetted by saline solution to prevent water evaporating. Removing the leptomeninges and blood, cutting and taking the front half portion of brain tissue centered by the hole for the insertion needle, weighing precisely (accurate to 0.1 mg). It is controlled in 5 min to take the brain to finish weigh. Then putting in 95° C. constant temperature oven for 24 h, weighing the dry weight. The brain water content is calculated according to Blliot formula: BWC=(wet weight−dry weight)/wet weight×100%.

TABLE 13 the influence of piperphentonamine hydrochloride on brain water content at 4 h, 8 h, 12 h, 24 h after cerebral hemorrhage in rats (x ± SD, n = 6)

| Experiment groups | brain water content (%) | | | |
|---|---|---|---|---|
|  | 4 h | 8 h | 12 h | 24 h |
| Sham | 70.74 ± 0.47 | 71.85 ± 0.58 | 73.28 ± 0.66 | 73.22 ± 0.88 |
| ICH | 80.17 ± 0.53$^{\Delta\Delta}$ | 81.60 ± 0.54$^{\Delta\Delta}$ | 83.39 ± 0.73$^{\Delta\Delta}$ | 79.05 ± 0.46$^{\Delta\Delta}$ |
| ICH + JBTA (2 mg/kg) | 79.29 ± 0.69* | 79.73 ± 0.53$^{\Delta**}$ | 80.75 ± 0.19$^{\Delta\Delta**}$ | 82.38 ± 0.73$^{\Delta\Delta**}$ |
| (0.5 mg/kg) | 79.90 ± 0.84$^\Delta$ | 81.19 ± 0.78$^{\Delta\Delta}$ | 82.70 ± 0.76$^{\Delta\Delta}$ | 84.98 ± 0.65$^{\Delta\Delta}$ |
| ICH + Nim (0.5 mg/kg) | 79.31 ± 0.76* | 79.95 ± 0.36$^{\Delta**}$ | 81.35 ± 0.71$^{\Delta\Delta**}$ | 82.89 ± 0.68$^{\Delta\Delta**}$ |

Note:
*P < 0.05,
**P < 0.01 VS model group;
$^\Delta$p < 0.05,
$^{\Delta\Delta}$p < 0.01 VS sham.

3.3 Histopathological Observation

Influence of piperphentonamine hydrochloride on pathological morphology of cerebral hemorrhage in rats was observed. Each group animals were selected randomly, anesthetized deeply by chloral hydrate at predetermined time point, decollated and the brain were taken out rapidly, then, the brain tissue slices with hematoma (about 5 mm) were cut, and put into 10% formaldehyde solution immediately, fixed for 24 h followed by dehydration by graded ethanol, transparentizing by xylene, immersing in paraffin, embedding, slicing (5 μm), HE staining and sealing. The pathological changes area and the pathological change of the adjacent brain tissue were observed by optical microscope.

Results: brain tissue of rats showed obvious pathological changes after cerebral hemorrhage, it could be observed on the sections at 4, 8, 12 hours that, there were obvious bleeding lesions, tissue around lesions was loose and dropsical, with some inflammatory cell infiltration; it could be observed on the sections at 24 hours that, tissue around lesions remain was loose and dropsical, inflammatory cell infiltration was more serious. The tissue edema and inflammatory cell infiltration after cerebral hemorrhage were reduce obviously in ICH rats pretreated with large dose of piperphentonamine hydrochloride; and administration with small doses of piperphentonamine or nimodipine in advance also could ease the pathological changes above-mentioned in different levels.

3.4 The Influence on the NE in Cerebra Tissue

Rats in each group were anesthetized by chloral hydrate, decollated rapidly and the brains were taken out. The brain tissue around the hole was cut and procured, weighed precisely, and made into a 10% tissue homogenate using a glass homogenizer in an ice bath environment with physiological saline as homogenized medium, the supernatant of which was taken to be determined the NE activity using ELISA method.

Results: compared to the sham operation group, brain tissue NE activity was increased significantly after cerebral hemorrhage of rat ($P<0.01$); high and low dose group of piperphentonamine hydrochloride could decrease the brain tissue NE activity significantly after cerebral hemorrhage of rats ($P<0.01$) (see table 14).

TABLE 14 the influence of piperphentonamine hydrochloride on the content of NE of tissue of ICH rat brain (x ± SD)

| Experiment group | n(samples) | NE(ng/ml) |
|---|---|---|
| Sham | 6 | $0.106 \pm 0.026^\Delta$ |
| ICH (24 h) | 6 | $2.08 \pm 0.062$ |
| ICH + JBTA - 2 mg/kg | 6 | $1.61 \pm 0.044^a$ |
| ICH + Nim - 0.5 mg/kg | 6 | $1.88 \pm 0.035^a$ | note:
$^\Delta P < 0.01$,
$^a P < 0.01$ VS model 3.5 The Influence on NO in Brain Tissue Rats in each group were anesthetized by chloral hydrate, decollated rapidly and the brain take were taken out. The brain tissue around the hole was cut and procured, weighed precisely, and made into a 10% tissue homogenate using a glass homogenizer in an ice bath environment with physiological saline as homogenized medium, the supernatant of which was taken to be determined the content of NO by nitrate reductase method.

Results: compared to the sham operation group, NO content in brain tissue of rats was increased significantly after cerebral hemorrhage ($P<0.01$). High and low dose groups of piperphentonamine hydrochloride could decrease the NO content in brain tissue of rats after cerebral hemorrhage.

TABLE 15 the influence of piperphentonamine hydrochloride on the content of NO in ICH rat brain tissue (x ± SD)

| Experiment group | n(samples) | NO(μmol/g pro) |
|---|---|---|
| Sham | 6 | $1.61 \pm 0.07^\Delta$ |
| ICH | 6 | $2.46 \pm 0.04$ |
| ICH + JBTA(2 mg/kg) | 6 | $1.65 \pm 0.03^\Delta$ |
| ICH + Nim(0.5 mg/kg) | 6 | $2.40 \pm 0.05^\Delta$ | note:
$^\Delta P < 0.01$ VS model

The invention chose intracerebral hemorrhage model of rats induced by collagenase as the research object, uses nimodipine which is commonly used in present clinical treatment of cerebral hemorrhage as comparative reference, to study the protective effect of piperphentonamine hydrochloride on cerebral hemorrhage. By contrastively observing the behavior change, pathology, brain water content change of ICH rat after administering, it was proved that piperphentonamine hydrochloride has protective effects on cerebral hemorrhage.

The other animal experiment results of the invention also showed that the piperphentonamine hydrochloride (2 mg/kg) can reduce increased degree of the BBB permeability of cerebral hemorrhage side of ICH rat brain induced by collagenase; can prevent the decrease of SOD content and the increase MDA content of cerebral hemorrhage side of the ICH rat brain induced by collagenase, and can reduce the expression of TNF-Q and the increase of MPO content of cerebral hemorrhage side of the ICH rat brain induced by collagenase. It was revealed that piperphentonamine hydrochloride may realize the protective effects of rat ICH induced by collagenase by the mechanisms of protecting BBB of ICH rats, improving the tissue ability of scavenging free radicals and resisting the aggregation of polymorphonuclear granulocyte, releasing the inflammatory mediators, etc.

Example 9

Piperphentonamine Hydrochloride Combined with Other Drugs was Used for the Treatment of Cerebral Ischemia Model preparation, administer method and index determination were the same as that of example 6. Piperphentonamine hydrochloride (JBTA) combining NGF, Vit B6 were used to treat the cerebral ischemia. The dose of piperphentonamine hydrochloride was 1 mg/kg iv, NGF 250 U, Vit B6 dose of 0.2 mg/kg IV were intramuscular injected immediately after brain injury of rats.

The results were as follows:

TABLE 16 the influence of medicine combination of JBTA on the treatment for local cerebral ischemia rats (x ± SD, n = 10)

| groups | Behavior disorder | Ischemia area(mm$^2$) |
|---|---|---|
| Sham operation | 0 | 0 |
| cerebral ischemia model | $12.43 \pm 3.55$ | $32.58 \pm 5.42$ |
| Nim | $8.31 \pm 1.98^*$ | $25.68 \pm 5.99^*$ |
| JBTA | $7.25 \pm 2.83^*$ | $20.64 \pm 4.85^*$ |
| JBTA + NGF + Vit B6 | $5.14 \pm 1.86^{*▲}$ | $15.27 \pm 3.11^{*▲}$ |

Compared to model group $^*P < 0.01$,
Compared to JBTA group $^▲P < 0.01$

The results suggested that the effect of piperphentonamine hydrochloride combined with other drugs was better.

Example 10

The Therapeutic and Protective Effect of Piperphentonamine Citrate on Closed Treatment of Traumatic Brain Injury of Mice Piperphentonamine citrate was diluted by 5% glucose injection for using. Automatic recorder of Diving platform experiment (electric instrument room of Chinese Academy of Medical Sciences Medicine Institute); fluorescence spectrophotometer (Japanese company HITACHI); Microplate reader (Molectlla, USA).

Experimental animal: Kunming mice of clean grade, with weight of 20 g-22 g.

The grouping method, administer method and model preparation were referred to example 2. The results were shown in Table 17. Cerebra oedema of the mouse was caused by closed cerebral trauma, which was relieved in varying degrees after being given different doses of piperphentonamine citrate, with dose dependent.

TABLE 17 the influence of piperphentonamine citrate on closed traumatic brain injury brain edema of mice (x ± SD, n = 10)

| groups | | Brain water content (%) |
|---|---|---|
| Normal control | | 74.92 ± 6.36** |
| Model group | | 89 ± 8.56 |
| Piperphentonamine citrate | 2 mg/kg | 80.32 ± 7.72* |
| | 4 mg/kg | 78.84 ± 9.48** |
| | 8 mg/kg | 75.28 ± 6.48** |

Compared to model group,
*$P < 0.05$,
**$P < 0.01$

Example 11

This embodiment relates to a use of piperphentonamine citrate for treatment of ischemia reperfusion of ischemic cerebrovascular disease in animal experiment.

The local cerebral ischemia reperfusion injury model was build by using mice thread bolt method, to prove that the JBAT citrate has protective effect on cerebral ischemia of experimental animals.

Method of making model was the same as example 7, the results showed that ischemic brain infarction area of the piperphentonamine citrate treated group (C) was reduced significantly, it was very significant difference compared to the operation group ($P<0.01$), as shown in table 18.

TABLE 18 the influence of piperphentonamine citrate on cerebral ischemia infarction area of mouse (x ± SD)

| groups | n | The percentage of infarction area occupied the entire coronal plane (%) |
|---|---|---|
| Sham operation (A) | 8 | 0 |
| ischemia reperfusion groups (B) | 8 | 25.35 ± 2.1* |
| treated group (C) | 8 | 16.88 ± 2.48**△△ |

Compared to the operation group,
**$P < 0.01$; Compared to the ischemia reperfusion group,
△△$P < 0.01$ The results showed that piperphentonamine citrate has a significant protective effect on cerebral infarction caused by cerebral ischemia/reperfusion injury of mice.

Example 12

The Protective Effects of Piperphentonamine Maleate on Cerebral Hemorrhage of Rats, Preventive Medicine Experimental animal: male Wistar rats, male and female in half, weight 180~250 g, 12 hours preoperative fasting food, drink water free.

1. Experimental Animals Groups

Divide the animals randomly into five groups: sham operation (sham) 24 h group; ICH+normal saline group (model); ICH+piperphentonamine maleate (4 mg/kg) group, namely high dose group (h); ICH+piperphentonamine maleate (2 mg/kg) group, namely low dose group (l); ICH+nimodipine (0.5 mg/kg) group. The last four groups were divided into four time subgroup of 4 h, 8 h, 12 h and 24 h. Physiological solution, piperphentonamine maleate and nimodipine were injected intravenous from rat tail vein 30 minutes before the ICH model made, once a day. Inject slowly, the total amount of drug liquid was controlled in 1 ml/200 g body weight: normal saline was also administered in 1 ml/200 g body weight. Each group has seven Wistar rats.

2. ICH Model of Rat

This article referred to the method reported by Rosenberg, etc. The specific operation was the same as above-mentioned.

Statistical processing: measured values of each group were expressed by mean+SD (x+SD); single factor analysis of variance (one-way ANOVA) was processed by using SPSS statistics software, with significant level $P<0.05$.

3. Observational Index and Results (1) The Influence of Piperphentonamine Maleate on Neurology Score of ICH Rats Nerval defect score standard is the same as example 9.

Results: the nerval defect scores of sham operation group was 0 points at each time point; the animals of model group were scored immediately after anesthesia as 3 or 4 points. On one hand, it was revealed that the ICH rat model establishment is successful, on the other hand, it was revealed that ICH result in a very obvious defect on rat neural function. At the same time we observed that the neural function score of each group of ICH rat was decreased gradually over time, wherein the score of drug administered group was decreased faster than the model group. There was significant difference of the score ratio of nerve defect of the group of being administered with large dose of piperphentonamine maleate at 12 h, 24 h after ICH, and model group, small dose of piperphentonamine maleate groups which are at the corresponding time point ($P<0.05$). There was significant difference in the score ratio of the nerve defect of nimodipine group at 12 h, 24 h after ICH and model group at the corresponding point time ($P<0.05$). The observations above suggested that intravenous administration of piperphentonamine maleate in 4 mg/kg can improve the nerve deficit score after ICH, whose effect was better than that of the 0.5 mg/kg nimodipine.

TABLE 19 the influence of piperphentonamine maleate on neurological scores at 4 h, 8 h, 12 h, 24 h after cerebra hemorrhage in rats (x ± SD, n = 7)

| | neurological score | | | |
|---|---|---|---|---|
| Experiment group | 4 h | 8 h | 12 h | 24 h |
| Sham | 0 | 0 | 0 | 0.00 |
| model | 3.77 ± 0.83 | 103.2 ± 0.83 | 3.25 ± 1.14 | 2.75 ± 0.91 |

TABLE 19-continued the influence of piperphentonamine maleate on neurological scores at 4 h, 8 h,
12 h, 24 h after cerebra hemorrhage in rats (x ± SD, n = 7)

| Experiment group | neurological score | | | |
|---|---|---|---|---|
| | 4 h | 8 h | 12 h | 24 h |
| piperphentonamine maleate (4 mg/kg) | 3.25 ± 0.59 | 3.08 ± 0.95 | 1.88 ± 0.64*$^\Delta$ | 1.37 ± 0.46**$^{\Delta\Delta}$ |
| piperphentonamine maleate (2 mg/kg) | 3.61 ± 0.7 | 3.43 ± 0.82 | 2.92 ± 0.95 | 2.57 ± 1.28 |
| nimodipine | 3.65 ± 0.8 | 3.25 ± 0.91 | 2.05 ± 0.91* | 1.55 ± 0.59**$^\Delta$ | note:
*P < 0.05,
**P < 0.01 VS model;
$^\Delta$P < 0.05,
$^{\Delta\Delta}$P < 0.01 VS nimodipine 2) Brain Water Content (BWC) Determination Results: it can be found by analyzing table 13 that, the rats brain water content at 4 h, 8 h, 12 h, 24 h time point after cerebral hemorrhage was increased obviously compared with sham operation group, and it has significant difference (P<0.05). The brain water content was increased incessantly with the time progressing, and achieved a peak at 24 hours after cerebral hemorrhage. The brain water content of ICH rat in treatment group was decreased in different degree compared with the model groups at each time point.

There was significant difference in the decrease of the brain water content of the group administered with large doses of piperphentonamine maleate compare with the model group at the four corresponding time point (P<0.05), and the decrease extent of the brain water content of the group administered with piperphentonamine maleate was quite larger compared with the nimodipine group at the four corresponding time point, but the difference was not significant (P>0.05). The decrease extent of the brain water content of the group of Nimodipine at the four corresponding time point is significant compared with the model group (P<0.05). The results suggested that, the administration of piperphentonamine maleate of 4 mg/kg can reduce the serious degree of rat cerebral edema after ICH, with similar therapeutic effect compared with 0.5 mg/kg nimodipine.

(3) The Histopathological Observation

Results: there was obvious pathological change in brain tissue of rats after cerebral hemorrhage. It could be observed on the sections at 4, 8, 12 hours that, there were obvious bleeding lesions, loose and dropsical tissue around lesions, with some inflammatory cell infiltration; it could be observed on the sections at 24 hours that, tissue around lesions remain loose and dropsical, inflammatory cell infiltration is more serious. Pretreatment with large dose of piperphentonamine maleate to the ICH rats could obviously reduce tissue edema and inflammatory cell infiltration after cerebral hemorrhage; and administration with small dose of piperphentonamine maleate or nimodipine in advance also could ease the pathological changes above-mentioned in different levels.

(4) Effects on Brain Tissue NE

Results: compared with the sham operation group, brain tissue NE activity was increased significantly after cerebral hemorrhage of rat (P<0.01); high dose group and low dose group of piperphentonamine maleate could decrease the brain tissue NE activity significantly after cerebral hemorrhage of rats (P<0.01) (see table 14).

TABLE 20 the influence of piperphentonamine maleate on brain water content at 4 h, 8 h,
12 h, 24 h after cerebral hemorrhage of rats (x ± SD, n = 6)

| Experiment group | brain water content | | | |
|---|---|---|---|---|
| | 4 h | 8 h | 12 h | 24 h |
| Sham | 60.01 ± 0.31 | 62.01 ± 0.36 | 62.99 ± 0.42 | 63.22 ± 0.58 |
| model | 62.88 ± 0.42$^{\Delta\Delta}$ | 64 ± 0.42$^{\Delta\Delta}$ | 65.41 ± 0.49$^{\Delta\Delta}$ | 66.36 ± 0.67$^{\Delta\Delta}$ |
| piperphentonamine maleate (4 mg/kg) | 62.19 ± 0.54* | 62.53 ± 0.42$^\Delta$** | 63.38 ± 0.15$^{\Delta\Delta}$** | 64.62 ± 0.58$^{\Delta\Delta}$** |
| piperphentonamine maleate (2 mg/kg) | 62.66 ± 0.66$^\Delta$ | 63.88 ± 0.55$^{\Delta\Delta}$ | 64.86 ± 0.59$^{\Delta\Delta}$ | 66.33 ± 0.5$^{\Delta\Delta}$ |
| nimodipine 0.5 mg/kg | 62.20 ± 0.59 | 62.70 ±0.25$^\Delta$ | 63.8 ± 0.56$^{\Delta\Delta}$ | 65.02 ± 0.54$^{\Delta\Delta}$ | note:
*P < 0.05,
**P < 0.01 VS model;
$^\Delta$P < 0.05,
$^{\Delta\Delta}$P < 0.01 VS sham.

TABLE 21

The influence of piperphentonamine maleate on the
content of NE of ICH rat brain tissue (x ± SD)

| Experiment group | n(samples) | NE(ng/ml) |
| --- | --- | --- |
| sham | 6 | 0.16 ± 0.04ΔΔ |
| Model (24 hours) | 6 | 3.07 ± 0.09 |
| piperphentonamine maleate-h | 6 | 2.37 ± 0.07ΔΔ |
| piperphentonamine maleate-l | 6 | 2.78 ± 0.05ΔΔ | note:
ΔΔ$p < 0.01$ VS model (5) The Influence on NO in Brain Tissue

Results: compared with the sham operation group, NO content in brain tissue of rats was increased significantly after cerebral hemorrhage ($P<0.01$). high dose group and low dose group of piperphentonamine maleate could decrease the NO content in brain tissue of rats after cerebral hemorrhage ($P<0.01$).

TABLE 22

The influence of piperphentonamine maleate on the
content of NO in ICH rat brain tissue (x ± SD)

| Experiment group | n(samples) | NO(μmol/g pro) |
| --- | --- | --- |
| Sham | 6 | 1.44 ± 0.06Δ |
| model | 6 | 2.21 ± 0.04 |
| piperphentonamine maleate (4 mg/kg) | 6 | 1.48 ± 0.03Δ |
| piperphentonamine maleate (2 mg/kg) | 6 | 2.16 ± 0.05Δ |

Note:
Δ$P < 0.01$ VS model

Piperphentonamine maleate (4 mg/kg) could promote the restoration process of behavior change of ICH rats induced by collagenase; relieve the occurring of cerebral edema with a dose-dependent manner; reduce the NE activity of cerebral tissue and NO content, at the same time, piperphentonamine maleate could reduce the pathological injury of cerebral cells in cerebral hemorrhage side of the brain of ICH rat. It was revealed that piperphentonamine maleate has protective effects on ICH of rat induced by collagenase.

Example 13

This embodiment relates to in vivo experiment of piperphentonamine maleate for the treatment of cerebral hemorrhage.

Adult male SD rats were divided randomly into normal saline group, cerebral hemorrhage group and piperphentonamine maleate group. A model of cerebral hemorrhage was established by the methods of injecting 50 μl autologous blood into caudate nucleus of rats, wherein, the position of caudate nucleus was determined according to "the rat cerebral in stereotaxic atlas": the injection position is at the point of front to anterior fontanelle of 0.2 mm, right to the sagittal suture of 3.0 mm, depth of 6.3 mm. The change of cerebral edema was observed by the dry-wet weight method; the behavior was observed by forelimb placement experiment. The cerebral hemorrhage group was only injected without medicine, with the treatment time of at 3 h after hemorrhage. The edema measurement time was in 1, 2, 3, 7, 14 days after hemorrhage, the behavioral observation time phase was in 1, 2, 3, 7, 14, 28 days after hemorrhage, each group of each time phase had 6 rats.

The research showed that, there was a close temporal correlation between hemorrhage cerebral edema and neurological function defect score: neurological function defect of cerebral hemorrhage group of rats was the most severe in 2 to 3 days after the operation, which was gradually recovered as time pass by (after hemorrhage 28 d>50%), which was related to the severe brain injury induced by the cerebral edema reaching to the peak 2~3 days after operation. Brain water content of cerebral hemorrhage group and piperphentonamine maleate group were compared with the normal saline group at 24 h, 48 h, 72 h ($P<0.05$), with no significant difference in 7 day ($P>0.05$) among each groups. Results of cerebral hemorrhage rat forelimb placement experimental was compared with the results of normal saline group ($P<0.05$), the Malay acid piperphentonamine group compare with cerebral hemorrhage group ($P<0.05$). The extent of edema reached a peak 24~48 h after cerebral hemorrhage. Piperphentonamine maleate could obviously relieve cerebral edema after cerebral hemorrhage, and improve the neural function defect after cerebral hemorrhage at the same time. Compared with the cerebral hemorrhage group at the same time, local administering with piperphentonamine maleate at ultra early stage (hemorrhage after 3H) could significantly reduce the early cerebral edema, improve neurological defect in long-term (1~28 days), reduce disability rate after hemorrhage, improve the prognosis by protecting the biofilm system.

Example 14

The embodiment relates to in vivo experiment of piperphentonamine acetate for the treatment of infectious brain edema.

Thirty SD rats weighing about 210 g were randomly divided into 3 groups: normal saline control group (NS, n=10); pertussis bacterial liquid model group (PB, n=10); pertussis bacterial liquid model group pretreated with piperphentonamine acetate (JBTA-H, n=8).

Model preparation was same as that of example 4. Piperphentonamine acetate group was intraperitoneally injected with 0.5 mg/kg daily for 2 days 48 h before the injection of pertussis bacterial liquid. Rats in each group were decollated after being injected with bacterial liquid or saline 4 h. ELISA method and Griess method were used to measure the content of IL-1β, TNF-α and NO in brain homogenate of infectious brain edema model of rats.

Pretreatment with piperphentonamine acetate could reduce brain water and sodium ion content of brain edema of pertussis bacterial liquid in rats significantly, increase the content of potassium ion, which indicated that pretreatment with piperphentonamine acetate have protection function on infectious brain edema in rats.

TABLE 23 brain water content and sodium and potassium ion changes after
the pretreatment with piperphentonamine acetate (x ± SD)

| groups | numbers | brain water content (%) | Na$^+$(nmol/kg) | K$^+$(nmol/kg) |
| --- | --- | --- | --- | --- |
| NS | 10 | 62.88 ± 0.24 | 155.4 ± 5.68 | 357.3 ± 8.88 |
| PB | 10 | 65.76 ± 0.24[1] | 221.6 ± 14.8[1] | 286.7 ± 20.0[1] |
| JBTA-H | 10 | 63.44 ± 0.4[3] | 164.7 ± 23.7[3] | 396.6 ± 39.9[3,2] | notes:
compared with NS:
[1]$P < 0.01$,
[2]$P < 0.05$; compared with PB
[3]$P < 0.01$.

The content of IL-1β, TNF-α and NO of the group pretreated with piperphentonamine acetate was reduced significantly (P<0.01), the results are showed in table 24.

TABLE 24

The content of IL-1β, TNF-α and NO in rat brain tissue after the pretreatment of piperphentonamine acetate (x ± SD)

| groups | IL-1β(pg/g) | TNF-α(pg/g) | NO(nmol/g) |
| --- | --- | --- | --- |
| NS | 157.3 ± 43.6 | 217.1 ± 49.7 | 47.39 ± 5.2 |
| PB | 249.6 ± 24.5[1] | 495.4 ± 55.1[1] | 68.9 ± 8.97[1] |
| JBTA-H | 197.1 ± 27.1[2)3] | 309.3 ± 83.5[2)3] | 53.3 ± 3.71[2)3] |

Notes:
[1]compared with NS group
[1]P < 0.01,
[2]compared with NS group P < 0.05,
[3]compared with PB group P < 0.01

The invention disclosed that content of IL-1β, TNF-α and NO in brain tissue was decreased significantly in infectious cerebral edema model of rats pretreated by piperphentonamine acetate, compared with infectious cerebral edema model without pretreated, while the brain water content, content of Na+ decrease, content of K+ were increased. Compared with the model group, the difference was significant (P<0.01). It revealed that piperphentonamine acetate can reduce the generation amount of IL-1β, TNF-α and NO, which has protective function on infectious brain edema of rats.

Example 15

The embodiment relates to in vivo experiment of piperphentonamine acetate for the treatment of ischemia reperfusion of cerebrovascular disease.

The local cerebral ischemia model of mice was established by using thread bolt method, to validate that piperphentonamine acetate has protective effect on experimental cerebral ischemia animal.

TABLE 25

The comparison of cerebral infarction area of cerebral ischemia model mice of each experimental groups of (x ± SD)

| groups | n | The percentage of infarction area occupied the entire coronal plane (%) |
| --- | --- | --- |
| Sham operation (A) | 8 | 0 |
| Operation group (B) | 8 | 27.04 ± 2.24 |
| Medicine group (C) 4 mg/kg | 8 | 18.12 ± 2.64^ΔΔ |

^ΔΔP < 0.01 VS B

Results showed that piperphentonamine acetate has significant protective effect on cerebral ischemia/reperfusion injury of mouse induced by cerebral infarction.

Example 16

The embodiment relates to the in vivo experiment of piperphentonamine hydrochloride HforH HinjectionH for treatment of ischemia reperfusion of ischemic cerebrovascular disease.

The formulation and process of piperphentonamine hydrochloride lyophilized preparation of the present embodiment are as follows:

| Formulation (5 ml/bottle × 1000 bottles): | |
| --- | --- |
| Raw medicine of Piperphentonamine hydrochloride | 10.0 g |
| Mannitol | 100.0 g |
| Adding injection water modulated to pH 3 by HCl to 5000 ml | |

The prepared, packed piperphentonamine hydrochloride preparation was put into sample chamber of freeze drying box→was pre-freezed at −30° C.→was sublimation dried at −15° C.→was dried again at 25° C.→was pressed with plug automatically→was capped with aluminum cap→was capped→was quality inspected.

Finished products were checked up according to quality inspection standards of piperphentonamine hydrochloride for injection, which should comply with the provision.

Model preparation and method of administering is the same as that of example 7, the results is showed in table below:

TABLE 26

The comparison of cerebral infarction area of cerebral ischemia model mice of each experimental groups of (x ± SD)

| groups | n | The percentage of infarction area occupied the entire coronal plane (%) |
| --- | --- | --- |
| Sham operation (A) | 8 | 0 |
| ischemia reperfusion (B) | 8 | 26.70 ± 2.21 |
| PPTA (C) | | |
| 1 mg/kg | 8 | 19.78 ± 2.61** |
| 5 mg/kg | 8 | 16.55 ± 2.32** |
| ATP (D) | | |
| 5 mg/kg | 8 | 20.53 ± 4.82* |
| Edaravone Injection (E) | | |
| 3 mg/kg | 8 | 18.43 ± 3.56** |

*P < 0.05,
**P < 0.01 VS B

The results show that piperphentonamine hydrochloride has significant protective effect on cerebral ischemia/reperfusion injury of mouse induced by cerebral infarction, and the effect is better than the ATP and edaravone.

Example 17

The embodiment relates to clinical therapeutical effect of piperphentonamine hydrochloride for injection on the treatment of stroke. The preparation of piperphentonamine hydrochloride for injection of this embodiment is same as Example 16.

The above accredited piperphentonamine hydrochloride for injection using in clinic, the results of treatment on acute ischemic stroke are as following:

Eighty patients with acute cerebral infarction are in hospital for treatment in 72 h after being taken bad, according with the Fourth National Academic Conference on cerebrovascular disease revised, removing cerebral haemorrhage by emergency cranial CT, 18 to 80 years old, male or female, no serious systemic complications, function of hepatic, renal is normal.

Eighty patients are divided into treatment group with 40 cases, control group with 40 cases, the difference of the patient's age, sex, infarct area and rating, etc, have no significance in statistics P>0.05.

The treatment group is administered piperphentonamine hydrochloride for injection 60 mg (1 mg/kg, Lot number 20080221), which is added into 5% glucose injection 250 ml, and intravenously dripped, for 2 h, twice a day, 14 d as a course.

The control group does not use piperphentonamine hydrochloride for injection, the rest treatment being same as the treatment group. In order to ensure the validity of data, it is not used such as mannitol, nimodipine, large dose, cytidine diphosphate choline, piracetam, etc.

Efficacy evaluation: it is evaluated by the neural function defect score (ESS) before medication, one week after medication, and two weeks after medication, judging the efficacy by score increased ratio.

Score increased ratio=[(score after treatment−scores before treatment)/score before treatment]*100%, it is determined the efficacy by dividing the increasing score ratio into 5 levels.

Score increased ratio of 80%-100% represents basic recovery, score increased ratio of 60%-80% represents significant progress, score increased ratio of 40%-60% represents progress, score increased ratio of less than 40% is invalidation, the efficacy rate is recorded by both basic recovery and significant progress.

Efficacy is compared among groups; significance test is carried by X2 test; the difference with P<0.05 is significance in statistics.

Two groups are scored to the patients before treatment, in 7 d after treatment, in 14 d after treatment, the results are showed in table 27.

chloride for injection treatment group is better than the one of control group, it has clinical significance.

In addition, it is researched that piperphentonamine or piperphentonamine hydrochloride in treating human brain and other diseases, and the results show that, it has obvious effect and clinical significance. It is also researched the other pharmaceutically acceptable piperphentonamine salts in treating human brain disease, and the results show that it has obvious effect.

What is claimed is:

1. A method for treating encephalopathy in a mammal subject, comprising the step of:
   administering an effective amount of a pharmaceutical composition comprising piperphentonamine or a piperphentonamine salt.

2. The method according to claim 1, wherein the piperphentonamine salt is piperphentonamine hydrochloride.

3. The method according to claim 2, wherein the piperphentonamine hydrochloride has a therapeutic concentration about 0.001 to about 0.08‰ of the mammal body weight.

4. The method according to claim 2, wherein the composition further comprises 5% by weight of glucose.

5. The method according to claim 1, wherein the piperphentonamine salt is piperphentonamine citrate.

6. The method according to claim 1, wherein the piperphentonamine salt is piperphentonamine maleate.

7. The method according to claim 1, wherein the piperphentonamine salt is piperphetonamine acetate.

8. The method according to claim 1, wherein said encephalopathy is cerebral injury disease or cerebrovascular disease.

9. The method according to claim 8, wherein said cerebrovascular disease is cerebral ischemia, cerebral ischemia/reperfusion injury or cerebral hemorrhage.

10. The method according to claim 9, wherein said cerebral hemorrhage is selected from the group consisting of hypertensive cerebral hemorrhage, cerebral hemorrhage secondary to infarction, tumor cerebral hemorrhage and cerebral hemorrhage caused by arteritis, wherein said cerebral ischemia is carotid system cerebral ischemia or vertebrobasilar cerebral ischemia.

TABLE 27

The clinical efficacy comparison of the patients in two groups before and after the treatment

| groups | Basic recovery (case) | | | significant progress (case) | | | Progress (case) | | | Invalidation (case) | | | efficacy rate % | | |
|---|---|---|---|---|---|---|---|---|---|---|---|---|---|---|---|
| | befor | in | after | befor | in | after | befor | in | after | befor | in | after | befor | in | after |
| Treatment group | 5 | 10 | 12 | 4 | 10 | 18 | 20 | 14 | 8 | 11 | 6 | 2 | — | 5% | 75% |
| control group | 5 | 8 | 10 | 5 | 8 | 10 | 20 | 12 | 15 | 10 | 12 | 5 | — | 40% | 50% |

X2 test is used for the comparison among groups, the total efficacy rate being 75%, being significantly better than 50% of the control group. The differences is significant in statistics P=0.001, compared between two groups, so it can be considered that therapeutic efficacy of piperphentonamine hydro-